United States Patent [19]
Lane et al.

[11] Patent Number: 5,770,365
[45] Date of Patent: Jun. 23, 1998

[54] NUCLEIC ACID CAPTURE MOIETIES

[75] Inventors: Michael J. Lane, Baldwinsville, N.Y.;
Albert S. Benight, Schaumburg, Ill.;
Brian D. Faldasz, Maynard, Mass.

[73] Assignee: Tm Technologies, Inc., Woburn, Mass.

[21] Appl. No.: 519,197

[22] Filed: Aug. 25, 1995

[51] Int. Cl.$^6$ .............................. C12Q 1/68; C07H 21/04; C07H 21/02

[52] U.S. Cl. .............................. 435/6; 536/24.3; 935/77; 935/78

[58] Field of Search .............................. 435/6; 536/24.3; 935/77, 78

[56] References Cited

U.S. PATENT DOCUMENTS

| | | | |
|---|---|---|---|
| 4,358,535 | 11/1982 | Falkow et al. | 435/5 |
| 4,563,419 | 1/1986 | Ranki et al. | 435/6 |
| 5,215,899 | 6/1993 | Dattagupta | 435/6 |
| 5,374,524 | 12/1994 | Miller | 435/6 |
| 5,503,980 | 4/1996 | Cantor | 435/6 |
| 5,556,752 | 9/1996 | Lockhart et al. | 435/6 |

OTHER PUBLICATIONS

Carpenter, W., "A Transcriptionally Amplified DNA Probe Assay with Ligatable Probes and Immunochemical Detection", *Clin. Chem.*, vol. 39, No. 9, pp. 1934–1938 (1993).

International Search Report dated Oct. 16, 1996, PCT/US96/13546.

Dunn et al., "A Novel Method to Map Transcripts: Evidence for Homology between an Adenovirus mRNA and Discrete Multiple Regions of the Viral Genome," *Cell*, 12:23–36 (1977).

Broude et al., "Enhanced DNA sequencing by hybridization," *Proc. Natl. Acad. Sci. USA*, 91:3072–3076 (1994).

Bell et al., "Polymeric DNA region adjacent to the 5' end of the human insulin gene," *Proc. Natl. Acad. Sci. USA*, 78:5759–5763 (1981).

Cantor and Schimmel, *Biophysical Chemistry*, W.H. Freeman and Company, San Francisco, Part III, pp. 1183–1264 (1980).

Doktycz et al., "Studies of DNA Dumbbells. IV. Preparation and Melting of a DNA Dumbbell with the 16 Base-Pair Sequence 5'G-T-A-T-C-C-C-T-C-T-G-G-A-T-A-C$^{3'}$ Linked on the Ends by Dodecyl Chains," *Biopolymers*, 33:1765–1777 (1993).

*Primary Examiner*—Stephanie W. Zitomer
*Assistant Examiner*—Paul B. Tran
*Attorney, Agent, or Firm*—Lahive & Cockfield, LLP; P. Louis Myers; Mark D. Russett

[57] ABSTRACT

Nucleic acid capture moieties, methods of using nucleic acid capture moieties, reaction mixtures including nucleic acid capture moieties, and kits including nucleic acid capture moieties are disclosed.

24 Claims, 9 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 19
        ( D ) OTHER INFORMATION: /note= "Biotinylated thymidine"

( i x ) FEATURE:
        ( A ) NAME/KEY: misc_feature
        ( B ) LOCATION: 38
        ( D ) OTHER INFORMATION: /note= "N represents between 4 and 50 additional bases."

( x i ) SEQUENCE DESCRIPTION: SEQ ID NO:1:

```
CTAGTCGACG TGGTCCTTTT TGGACCACGT CGACTAGN                      38
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 20
        ( D ) OTHER INFORMATION: /note= "Biotinylated thymidine"

( i x ) FEATURE:
        ( A ) NAME/KEY: misc_feature
        ( B ) LOCATION: 1
        ( D ) OTHER INFORMATION: /note= "N represents between 4 and 50 additional bases."

( x i ) SEQUENCE DESCRIPTION: SEQ ID NO:2:

```
NCTAGTCGAC GTGGTCCTTT TTGGACCACG TCGACTAG                      38
```

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
CAGCGCGTTT TAG                                                 13
```

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
CAGCGCGTTT TAGCTTA                                                                              17
```

( 2 ) INFORMATION FOR SEQ ID NO:5:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 19
        ( D ) OTHER INFORMATION: /note= "Biotinylated thymidine"

( x i ) SEQUENCE DESCRIPTION: SEQ ID NO:5:

```
CTAGTCGACG TGGTCCTTTT TGGACCACGT CGACTAGCTA AAACGCGCTG                                          50
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
TTATAATTAA CCGGTATATA                                                                           20
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
GGCGTTAACC AGCGCGTTTT AG                                                                        22
```

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
TACCGGAAGG AATTCTTCGT GCATG                                                                     25
```

(2) INFORMATION FOR SEQ ID NO:9:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:9:

ATTTTTTGCA AATTTTTATT TGCCCGAGTA TA    32

(2) INFORMATION FOR SEQ ID NO:10:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

TTATTTGCCC GAGTATA    17

(2) INFORMATION FOR SEQ ID NO:11:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:11:

ATTTTTTGCA AATTT    15

(2) INFORMATION FOR SEQ ID NO:12:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: modified_base
    (B) LOCATION: 34
    (D) OTHER INFORMATION: /note= "Biotinylated thymidine"

(xi) SEQUENCE DESCRIPTION: SEQ ID NO:12:

AAATTTGCAA AAAATCTAGT CGACGTGGTC CTTTTTGGAC CACGTCGACT AG    52

NUCLEIC ACID CAPTURE MOIETIES

BACKGROUND OF THE INVENTION

The present invention pertains to methods of detecting nucleic acid sequences.

Methods of detecting sequences of nucleic acids are of wide applicability in fields such as medical diagnosis.

In one prior art method, described, for example, in U.S. Pat. No. 4,358,535 to Falkow, the target nucleic acid is immobilized on a solid surface, such as a nitrocellulose filter. The target is then detected by hybridization with a labelled probe which is complementary to the target.

Other methods include those assays generally described as "sandwich assays", such as those disclosed by Dunn et al., *Cell* 12:33–36 (1977); and U.S. Pat. No. 4,563,419 to Ranki. In this format, a target nucleic acid is hybridized to a capture probe, and a second, reporter probe complementary to the target but not to the capture probe, is then added. Excess probes are washed away and binding of the reporter probe is measured. A solution sandwich assay is described in U.S. Pat. No. 5,374,524 to Miller.

Broude et al. (*Proc. Natl. Acad. Sci. USA* 91:3072 (1994)) have reported a nucleic acid capture system which uses an immobilized probe having single-stranded and duplex regions. This system was found to have increased sequence specificity compared to simple single-stranded probes.

SUMMARY OF THE INVENTION

The methods of the invention feature nucleic acid capture moieties which are complementary to a target sequence to sensitively and selectively detect target nucleic acid sequences.

In one aspect, the invention features a method of promoting the hybridization of a target single-stranded nucleic acid and a nucleic acid capture moiety, comprising:

a) providing a unimolecular nucleic acid capture moiety having a double-stranded region with a terminal base and an adjacent single-stranded region, a terminal base of the double-stranded region being all or part of a duplex-binding-ligand binding site, and the single-stranded region being capable of hybridizing to said target nucleic acid;

b) forming a reaction mixture comprising the target single-stranded nucleic acid, the nucleic acid capture moiety, and a duplex-binding ligand, under conditions such that the target single-stranded nucleic acid and the nucleic acid capture moiety can hybridize; and c) allowing the target single-stranded nucleic acid to hybridize to the nucleic acid capture moiety such that the duplex-binding ligand binds an intermolecular duplex thereby formed, whereby the hybridization of the target single-stranded nucleic acid and the nucleic acid capture moiety is promoted. In preferred embodiments, a first base pair of a duplex formed by the target single-stranded nucleic acid and the single-stranded region of the nucleic acid capture moiety encodes part of the duplex-binding-ligand binding site; the nucleic acid capture moiety comprises a nucleic acid hairpin; the nucleic acid capture moiety is bound to a solid support; base stacking between a terminal base of the nucleic acid capture moiety and a terminal base of the target single-stranded nucleic acid increases stability of the intermolecular duplex.

In another aspect, the invention features a method of detecting a target single-stranded nucleic acid sequence, comprising:

a) providing a nucleic acid capture moiety comprising a structure A-B-C-D wherein A is a nucleic acid sequence;

B and D are nucleic acid sequences which are capable of hybridizing to each other to form an intramolecular duplex; and C is a linker;

wherein A is substantially complementary to a target single-stranded nucleic acid sequence;

b) forming a reaction mixture comprising the target single-stranded nucleic acid and the nucleic acid capture moiety under conditions such that the target single-stranded nucleic acid and the nucleic acid capture moiety can hybridize; and c) detecting the presence or absence of hybridization of the target nucleic acid and the nucleic acid capture moiety;

whereby the target single-stranded nucleic acid is detected. In preferred embodiments, a terminal base of D comprises all or part of a duplex-binding-ligand binding site; the reaction mixture further comprises a duplex-binding ligand; the nucleic acid capture moiety is immobilized on an insoluble support; the duplex-binding ligand does not covalently modify any duplex; base stacking between a terminal base of the nucleic acid capture moiety and a terminal base of the target single-stranded nucleic acid increases stability of the intermolecular duplex.

In another aspect, the invention features a method of detecting a target single-stranded nucleic acid sequence, comprising:

a) providing a nucleic acid capture moiety comprising a structure A-B-C-D wherein A is a nucleic acid sequence;

B and D are nucleic acid sequences which are capable of hybridizing to each other to form an intramolecular duplex; and C is a linker;

wherein A is substantially complementary to a target single-stranded nucleic acid sequence;

b) forming a reaction mixture comprising the target single-stranded nucleic acid and the nucleic acid capture moiety under conditions such that the target single-stranded nucleic acid and the nucleic acid capture moiety can hybridize to form an intermolecular duplex, wherein the intermolecular duplex comprises a duplex-binding-ligand binding site; and c) detecting the presence or absence of hybridization of the target nucleic acid and the nucleic acid capture moiety;

whereby the target single-stranded nucleic acid is detected. In preferred embodiments, hybridization of the target single-stranded nucleic acid to the nucleic acid capture moiety forms a nicked duplex; the duplex-binding-ligand binding site does not include a nick; the reaction mixture further comprises a duplex-binding ligand; the duplex-binding ligand is sequence-specific; the duplex-binding ligand does not covalently modify any duplex; base stacking between a terminal base of the nucleic acid capture moiety and a terminal base of the target single-stranded nucleic acid increases stability of the intermolecular duplex.

In another aspect, the invention features a method of promoting the hybridization of a target single-stranded nucleic acid and a nucleic acid capture moiety comprising:

a) providing a unimolecular nucleic acid capture moiety having a double-stranded region and an adjacent single-stranded region, and the single-stranded region being capable of hybridizing to said target nucleic acid;

b) forming a reaction mixture comprising said target single-stranded nucleic acid, the nucleic acid capture moiety, and a duplex-binding ligand, under conditions such that the target single-stranded nucleic acid and the nucleic acid capture moiety can hybridize; and c) allowing said target single-stranded nucleic acid to hybridize to said nucleic acid capture moiety to form an intermolecular duplex, wherein the intermolecular duplex comprises a duplex-binding-ligand binding site, such that the duplex-binding ligand binds to the duplex-binding-ligand binding site, whereby the hybridization of the target single-stranded nucleic acid and the nucleic acid capture moiety is promoted. In preferred embodiments, the nucleic acid capture moiety comprises a nucleic acid hairpin; the nucleic acid capture moiety is bound to a solid support; the duplex-binding ligand does not covalently modify any duplex; the duplex-binding-ligand binding site does not include a nick; base stacking between a terminal base of the nucleic acid capture moiety and a terminal base of the target single-stranded nucleic acid increases stability of the intermolecular duplex.

In another aspect, the invention provides a nucleic acid capture moiety comprising a structure A-B-C-D wherein A is a nucleic acid sequence;

B and D are nucleic acid sequences which are capable of hybridizing to each other to form an intramolecular duplex; and C is a linker;

and where the nucleic acid capture moiety is immobilized on an insoluble support. In preferred embodiments, A is substantially complementary to a target nucleic acid sequence; base stacking between a terminal base of the nucleic acid capture moiety and a terminal base of the target single-stranded nucleic acid increases stability of an intermolecular duplex; the nucleic acid capture moiety is selected such that a duplex formed by hybridization of the target nucleic acid sequence to the nucleic acid capture moiety comprises a binding site for a pre-selected duplex-binding ligand.

In another aspect, the invention features a reaction mixture, comprising an immobilized hairpin, an insoluble support, and a target nucleic acid. In preferred embodiments, the hairpin is selected such that a duplex formed by hybridization of the target nucleic acid sequence to the hairpin comprises a binding site for a pre-selected duplex-binding ligand; the reaction mixture further comprises a duplex-binding ligand; the duplex-binding ligand is sequence-specific.

In still another aspect, the invention provides a kit for the detection of a target nucleic acid, the kit comprising an immobilized hairpin, an insoluble support, and a nucleic acid standard. In preferred embodiments, the kit further comprises a duplex-binding ligand.

DETAILED DESCRIPTION

Figure 1:
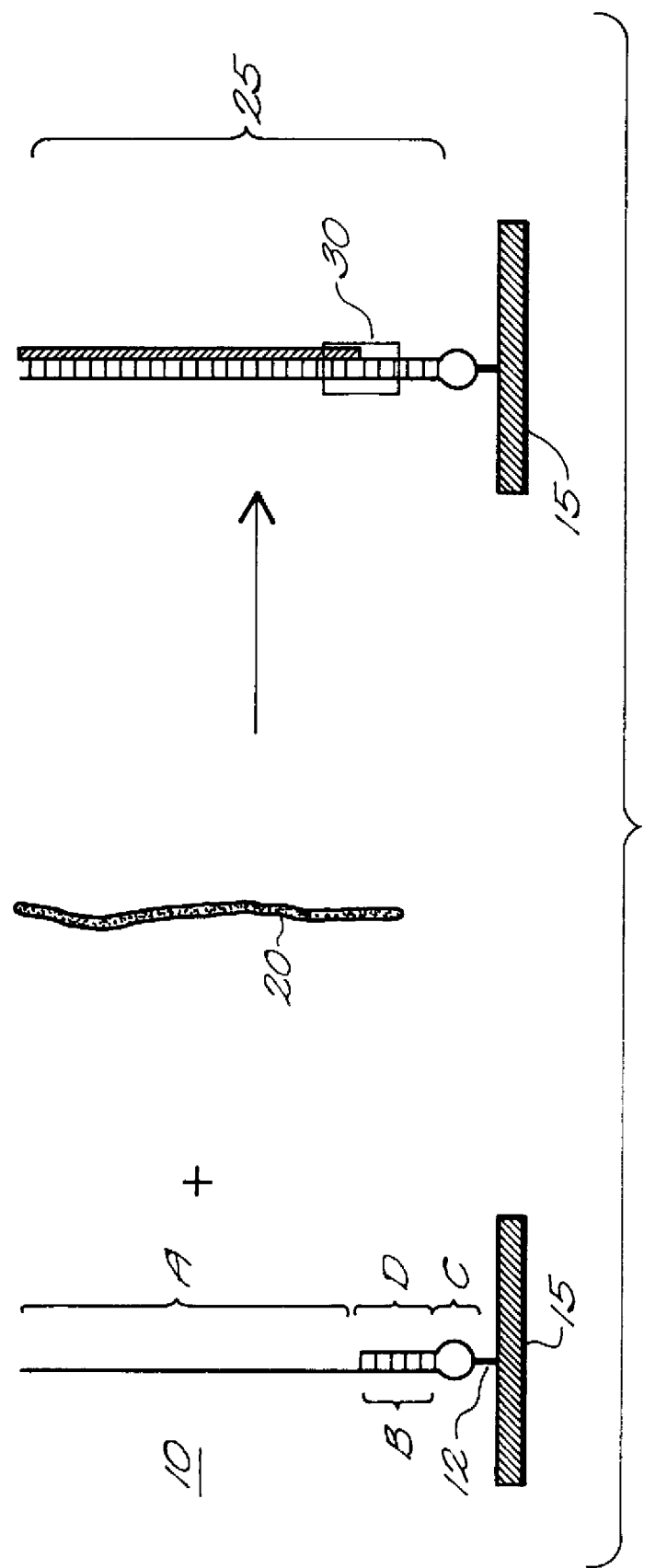
FIG. 1 is a reaction scheme showing capture of a target nucleic acid by a nucleic acid hairpin.

The methods of the invention are useful in the detection of nucleic acid sequences. The invention features novel nucleic acid capture moieties for use in detecting target nucleic acids. The methods of the invention can be performed with capture moieties immobilized in multiwell plates; thus, multiple samples can be screened simultaneously. Also, the methods of the invention can easily be automated, at least in part, to speed screening and improve economy. The capture moieties can selectively bind the target sequence, thereby reducing background noise to very low levels. An additional advantage is that the label signal can be amplified to achieve highly sensitive detection.

The term "nucleic acid strand", as used herein, refers to a strand of DNA or RNA, or a chimeric DNA-RNA strand, or nucleic acid-like compounds such as peptide nucleic acids. A nucleic acid strand can also include modified DNA or RNA bases, of which many are known in the art.

The term "target nucleic acid sequence" or "target strand" refers to a nucleic acid sequence which is to be detected. The target nucleic acid sequence can be any nucleic acid strand, as defined above, and in general will be single-stranded or will be made single-stranded by methods known in the art. The target nucleic acid sequence can be obtained from various sources including plasmids, viruses, bacteria, fungi, yeast, plants, and animals, including humans; or the target nucleic acid sequence can be obtained from non-natural sources. The target nucleic acid sequence can be obtained from various organisms or tissues, including fluids such as blood, semen, urine and the like. The target nucleic acid sequence is preferably extracted or purified to remove or reduce contaminating or interfering materials such as proteins or cellular debris. Procedures for such purification or extraction are known in the art, including, for example, those described in Maniatis et al., "Molecular Cloning: A Laboratory Manual", Cold Spring Harbor Laboratory (1989), or in Bell et al., *Proc. Nat. Acad. Sci. USA* (1981), 78:5759–5763. The methods and compositions of the present invention are particularly useful in the detection of nucleic acid sequences associated with infectious diseases, genetic disorders, or cellular conditions such as cancer. The methods of the invention are also useful for the detection of non-natural target nucleic acids, as described in more detail below.

The term "adjacent", as used herein, refers to non-overlapping segments of a nucleic acid strand which are not separated by intervening bases.

In one aspect, the invention features a nucleic acid capture moiety which has at least one nucleic acid region which is substantially complementary to a target nucleic acid, and having at least two nucleic acid regions which are capable of forming an intramolecular duplex. The term "nucleic acid capture moiety" or simply "capture moiety", as used herein, refers to a moiety which binds selectively to a target nucleic acid sequence and which can be immobilized on an insoluble support. The capture moiety can be immobilized on the solid support before, simultaneous with, or after capturing the target strand. A capture moiety can "capture" a target nucleic acid by hybridizing to the target and thereby immobilizing the target. In preferred embodiments, the nucleic acid capture moiety comprises a nucleic acid strand which has at least one region which is substantially complementary to a region of the target nucleic acid sequence. A preferred capture moiety is a nucleic acid hairpin, as defined below. In general, a capture moiety will be bound to a solid support. Such binding to a solid support may be through a linking moiety which is bound to either the capture moiety or to the solid support. In certain embodiments, the capture moiety may be labelled, as with, e.g., a radioisotope, a fluorescent moiety, an antibody, an antigen, a lectin, an enzyme, or other labels well known in the art. In embodiments in which the capture moiety does not contain a detectable label, the target nucleic acid sequence may be so labelled, or, alternatively, labelled secondary probes may be employed. A "secondary probe" is a nucleic acid sequence which is complementary to either a region of the target nucleic acid sequence or to a region of the capture moiety.

The terms "nucleic acid hairpin", "hairpin capture moiety", or simply "hairpin", as used herein, refer to a unimolecular nucleic acid-containing structure which comprises at least two mutually complementary nucleic acid regions such that at least one intramolecular duplex can form. Hairpins are described in, for example, Cantor and Schimmel, "Biophysical Chemistry", Part III, p. 1183 (1980). In certain embodiments, the mutually complementary nucleic acid regions are connected through a nucleic acid strand; in these embodiments, the hairpin comprises a single strand of nucleic acid. A region of the capture moiety which connects regions of mutual complementarity is referred to herein as a "loop" or "linker". In preferred embodiments, a loop comprises a strand of nucleic acid or modified nucleic acid. In preferred embodiments, the linker is not a hydrogen bond. In other embodiments, the loop comprises a linker region which is not nucleic-acid-based; however, capture moieties in which the loop region is not a nucleic acid sequence are referred to herein as hairpins. Examples of non-nucleic-acid linkers suitable for use in the loop region are known in the art and include, for example, alkyl chains (see, e.g., Doktycz et al. (1993) *Biopolymers* 33:1765). While it will be understood that a loop can be a single-stranded region of a hairpin, for the purposes of the discussion below, a "single-stranded region" of a hairpin refers to a non-loop region of a hairpin. In embodiments in which the loop is a nucleic acid strand, the loop preferably comprises 2–20 nucleotides, more preferably 3–8 nucleotides. The size or configuration of the loop or linker is selected to allow the regions of mutual complementarity to form an intramolecular duplex. In preferred embodiments, hairpins useful in the present invention will form at least one intramolecular duplex having at least 2 base pairs, more preferably at least 4 base pairs, and still more preferably at least 8 base pairs. The number of base pairs in the duplex region, and the base composition thereof, can be chosen to assure any desired relative stability of duplex formation. For example, to prevent hybridization of non-target nucleic acids with the intramolecular duplex-forming regions of the hairpin, the number of base pairs in the intramolecular duplex region will generally be greater than about 4 base pairs. The hairpin described in Example 3, infra, has a 16-base-pair duplex region, conferring exceptional stability on the intramolecular duplex. The intramolecular duplex will generally not have more than about 40 base pairs. In preferred embodiments, the intramolecular duplex is less than 30 base pairs, more preferably less than 20 base pairs in length.

A hairpin may be capable of forming more than one loop. For example, a hairpin capable of forming two intramolecular duplexes and two loops is referred to herein as a "double hairpin". In preferred embodiments, a hairpin will have at least one single-stranded region which is substantially complementary to a target nucleic acid sequence. "Substantially complementary" means capable of hybridizing to a target nucleic acid sequence under the conditions employed. In preferred embodiments, a "substantially complementary" single-stranded region is exactly complementary to a target nucleic acid sequence. In preferred embodiments, hairpins useful in the present invention have a target-complementary single-stranded region having at least 5 bases, more preferably at least 8 bases. In preferred embodiments, the hairpin has a target-complementary single-stranded region having fewer than 30 bases, more preferably fewer than 25 bases. The target-complementary region will be selected to ensure that target strands form stable duplexes with the capture moiety. In embodiments in which the capture moiety is used to detect target strands from a large number of non-target sequences (e.g., when screening genomic DNA), the target-complementary region should be sufficiently long to prevent binding of non-target sequences. A target-specific single-stranded region may be at either the 3' or the 5' end of the capture moiety strand, or it may be situated between two intramolecular duplex regions (for example, between two duplexes in a double hairpin).

In preferred embodiments, hairpins useful in the present invention have the structure A-B-C-D
wherein
A is a target-specific nucleic acid sequence;
B and D are nucleic acid sequences which are capable of hybridizing to each other to form an intramolecular duplex; and
C is a linker.

Thus, immobilized hairpins have the general structure illustrated in FIG. 1. The immobilized hairpin 10 has regions B and D which are mutually complementary and form an intramolecular duplex (also referred to herein as a "stem"). The region A of hairpin 10 forms a pendant single-strand, and is preferably selected to be, at least in part, substantially complementary to a target nucleic acid sequence. The linker C of hairpin 10 is a member which covalently or non-covalently links the nucleic acid sequences B and D together and positions them (e.g., holds them in sufficiently close proximity) such that a B:D intramolecular duplex can form. FIG. 1 illustratively shows the hairpin 10 immobilized to an insoluble support 15 through a spacer moiety 12. The linker C is also referred to herein as the "loop". In preferred embodiments, C covalently links B and D. In preferred embodiments, C is a nucleic acid sequence, but in other embodiments, C is not a nucleic acid sequence. In preferred embodiments, C is other than a solid or insoluble support. In other preferred embodiments, C is an insoluble support. FIG. 1 further shows the hybridization of a target strand 20 to the hairpin capture moiety 10, to form a nicked duplex 25. In FIG. 1, an optional duplex-binding-ligand binding site 30 is located at the nick in the target:capture moiety duplex, although a duplex-binding-ligand binding site may be absent or may be situated at locations which do not include a nick, as described in more detail below.

In particularly preferred embodiments, a hairpin will have at least one single-stranded region contiguous with a region which forms an intramolecular duplex, wherein the single-stranded region is substantially complementary to a target sequence. In an illustrative embodiment, the nucleic acid sequence A is a single-stranded region which is substantially complementary to a target sequence, and the nucleic acid sequence B is a region which forms an intramolecular duplex with region D. In particularly preferred embodiments, upon hybridization of the hairpin with a target nucleic acid sequence, a "nicked" duplex structure will be formed, comprising contiguous regions of intramolecular hairpin:hairpin duplex and intermolecular target:hairpin duplex. This arrangement provides several advantages. First, base stacking between the intramolecular duplex and the intermolecular duplex (i.e., between a terminal base of the target sequence and a terminal base of the capture moiety) provides greater sequence stringency than hybridization to a simple single strand, as described in Khrapko et al.(1991) *J. DNA Sequencing Mapping* 1:375–388. Second, as detailed below, the nicked duplex structure may include a duplex-binding-ligand binding site. In the presence of an appropriate duplex-binding ligand, the ability of the capture moiety to hybridize to the correct target sequence will be increased (e.g., the hybridization efficiency is increased), thus increasing the sensitivity of the assay. Furthermore, the use of a unimolecular capture moiety reduces experimental difficulties related to bimolecular moieties. For example, use of a unimolecular capture moiety requires fewer experimental steps than a bimolecular duplex, concentration dependence of duplex formation and stability is eliminated, an intramolecular duplex is more stable than the corresponding intermolecular duplex, and the like. Also, the duplex region of the capture moiety stabilizes (e.g., entropically) the target-specific region of the capture moiety and thereby favors formation of a target:capture moiety duplex. In a preferred embodiment, the region D of the capture moiety has a 3' or 5' terminal base; that is, a terminal base which is not linked to the loop region C. The terminal base will be at the 3' or 5' terminus of the region D, depending on the direction of the sequence (e.g., 5'–3' or 3'–5') of the region D. The nucleic acid sequence which ends in a terminal base is referred to herein as a "terminal sequence".

In preferred embodiments, the nucleic acid capture moiety is derivatized to allow binding to a solid support. Many methods of derivatizing a nucleic acid for binding to a solid support are known in the art. The capture moiety may be bound to a solid support through covalent or non-covalent bonds. In a preferred embodiment, the nucleic acid capture moiety is covalently bound to biotin to form a biotinylated conjugate. The biotinylated conjugate is then bound to a solid surface, for example, by binding to a solid, insoluble support derivatized with avidin or streptavidin. The capture moiety can be conveniently derivatized for binding to a solid support by incorporating modified nucleic acids in the loop region.

Thus, in a preferred embodiment, the capture moiety is derivatized in the loop region to permit binding to a solid support. In other preferred embodiments, the capture moiety is derivatized in a region other than the loop or linker region. For example, biotin-modified nucleic acids can be incorporating into the loop region to permit binding to a streptavidin-coated solid support. As noted above, a variety of moieties useful for binding to a solid support (e.g., biotin, antibodies, and the like), and methods for attaching them to nucleic acids, are known in the art. For example, an amine-modified nucleic acid base (available from, e.g., Glen Research) can be attached to a solid support (for example, Covalink-NH, a polystyrene surface grafted with secondary amino groups, available from Nunc) through a bifunctional crosslinker (e.g., bis(sulfosuccinimidyl suberate), available from Pierce). In another example, a sulfhydryl-functionalized hairpin (obtained by treating an amine-functionalized hairpin as described above with Traut's reagent (2-iminothiolane.HCl)) can be attached to a maleimide-coated polystyrene plate, available from, e.g., Corning-Costar. Additional spacing moieties can be added to reduce steric hindrance between the capture moiety and the surface of the solid support.

Thus, exemplary hairpin capture moieties include the two structures:

SEQ ID NO 1 and

SEQ ID NO 2 in which N represents any base, and n is an integer which will generally be between 4 and 50, more preferably between 5 and 30. These illustrative hairpins have been derivatized, with biotin, in the loop region for binding to a solid support, although such is not required.

In preferred embodiments, the solid support is a bead, more preferably a magnetic bead. Use of beads allows the derivatized nucleic acid capture moiety to be separated from a reaction mixture by centrifugation or filtration, or, in the case of magnetic beads, by application of a magnetic field. In other preferred embodiments, the nucleic acid capture moiety is bound to a surface such as a membrane or a reaction vessel, for example, a 96-well plate. As discussed more fully below, use of multi-well plates allows simultaneous screening for multiple target sequences using multiple hairpins, and also allows the use of automated equipment to perform the screening assays. Derivatization of surfaces to allow binding of the capture moiety is conventional in the art. For example, coating of surfaces with streptavidin allows binding of a biotinylated capture moiety. Coating of surfaces with streptavidin has been described in, for example, U.S. Pat. No. 5,374,524 to Miller.

In certain embodiments, it may be desired to use a plurality of hairpin sequences to detect a plurality of target sequences. In such embodiments, it is advantageous, although not required, to synthesize the hairpins with a constant region, which is the same for each hairpin and includes the loop and intramolecular duplex-forming regions, and a variable, target-specific region, which differs from one hairpin to the next according to the desired target sequence. One method of achieving this result is to synthesize a sufficient amount of the nucleic acid strand corresponding to the constant region, and then to add on the variable region appropriate for each target sequence by methods known in the art (e.g., chemical synthesis or ligation of a desired sequence).

In preferred embodiments, the capture moiety is selected such that upon hybridization with a target nucleic acid sequence, a nicked duplex (e.g., a duplex without gaps) is formed. This result may be achieved in various ways. For example, before contacting the target nucleic acid sequence with the capture moiety, the target nucleic acid may be treated with an agent, such as a restriction enzyme, which cleaves the target strand at a known, defined recognition sequence. Thus, the target nucleic acid sequence after cleavage will terminate with a known base or bases. The capture moiety and the restriction enzyme can be chosen to provide a nicked duplex upon hybridization of the capture moiety with the selectively cleaved target strand. Alternatively, the target strand may be "tailed" with a specific base or bases to provide a known terminal sequence. For example, the target strand may be modified by chemical (e.g., by phosphoramidite chemistry) or biochemical (e.g., polymerase extension or ligase-catalyzed ligation, when hybridized to a complementary strand) means to provide a known terminal sequence. It will be appreciated by the skilled artisan, however, that the duplex formed upon binding of the target strand to the capture moiety can, in some embodiments, have a gap or gaps.

In preferred embodiments, the capture moiety is selected such that when the target nucleic acid sequence hybridizes to the capture moiety, the target:capture moiety duplex thereby formed contains a binding site for at least one duplex-binding ligand. A duplex-binding ligand is a moiety which binds duplex nucleic acids in preference to single strands. Preferred duplex-binding ligands recognize (bind to) a recognition site (or binding site) of duplex nucleic acid, which is more strongly bound than non-recognition sites, and are referred to herein as "sequence-specific" duplex-binding ligands. Thus, in a preferred embodiment, the target:capture moiety duplex comprises a binding site for a sequence-specific duplex-binding ligand. In preferred embodiments, the duplex-binding ligand binding site binds a pre-selected duplex-binding ligand. Other preferred duplex-binding ligands do not exhibit site specificity and are referred to herein as "non-sequence-specific" duplex-binding ligands. Exemplary duplex-binding ligands include enzymes, such as restriction enzymes, polymerases, ligases, and the like; drugs such as actinomycin D; non-sequence-specific intercalaters such as ethidium bromide; and the like. In preferred embodiments, the duplex-binding ligand, whether sequence-specific or non-sequence-specific, does not covalently modify any duplex, e.g., does not create and/or cleave any covalent bond, e.g., a covalent bond of the capture moiety or the target nucleic acid. In preferred embodiments, the duplex-binding ligand is other than a ligase or a polymerase.

In other preferred embodiments, the target:capture moiety duplex comprises a binding site for a non-sequence-specific duplex-binding ligand.

The capture moiety may be selected such that the terminal base of an intramolecular duplex-forming region, when taken in combination with a terminal base of the target strand, forms a binding site for a duplex-binding ligand. In other words, the duplex-binding-ligand binding site includes the nick in the duplex formed by hybridization of the target to the capture moiety. For example, the duplex-binding-ligand Actinomycin D binds preferentially to the sequence 5'-AGCT-3'. Illustratively, the capture moiety may be chosen to have the 5'-terminal sequence 5'-CT- as part of an intramolecular duplex, and the target strand is selected (or modified) to have the 3'-terminal sequence -AG-3'. Thus, upon hybridization of the target strand to the capture moiety, the nicked duplex 5'-AG-CT-3' is formed, wherein the "G-C" represents the nick between G and C. This embodiment is particularly useful when discrimination between target sequences of differing length (e.g., cut and uncut targets) are used. If the longer target sequence forms an overhang when hybridized to the hairpin capture moiety, addition of a duplex-binding-ligand which has a recognition site which includes the nick site will improve discrimination between cut and uncut target sequences, as described in more detail below and in Examples 1 and 2.

The capture moiety can also be selected so that a duplex-binding-ligand binding site will form in a region which does not include an intramolecular duplex (e.g., the duplex-binding-ligand binding site does not include a nick). In preferred embodiments, the duplex-binding ligand binding site does not include any nick. For example, the target sequence may be selected to contain the sequence 5'-AGCT-3'. Thus, the target-specific region of the hairpin capture moiety will contain the complementary sequence, and Actinomycin D will recognize the duplex formed upon binding of the target strand to the capture moiety. The presence of the duplex-binding-ligand will increase the amount of target-:capture moiety duplex which is formed (by binding the duplex), thereby improving sensitivity.

The capture moiety can also be selected so that more than one duplex-binding-ligand binding site is formed upon binding of the target strand to the hairpin. The binding sites may be for a single duplex-binding ligand (for example, several actinomycin D binding sites), or for more than one ligand (e.g., an actinomycin D site and an EcoRI site). By adding the appropriate duplex-binding ligands, a desirable balance between detection sensitivity and target selectivity can be obtained.

It will also be recognized that duplex denaturing reagents can be used to increase the specificity of target binding to the capture moiety. In other words, a duplex denaturant can be used to destabilize duplex formation, particularly duplexes resulting from hybridization of mismatched nucleic acid sequences. Duplex denaturants include any means of favoring single strand formation and disfavoring duplex formation. Increased temperature (heating) may be used as a duplex denaturant, although this is not preferred. In preferred embodiments, a duplex denaturant is a chemical or biochemical reagent. Exemplary duplex denaturants include enzymes and proteins such as single-strand binding protein (e.g., from *E. coli*), the G-5 protein, the gene 32 protein, Rec A, and helicases, as well as chemical denaturants such as urea. Duplex denaturants can be identified by measuring the Tm of a duplex in the presence and the absence of a suspected duplex denaturant; a duplex denaturant will lower the Tm. Preferred duplex denaturants do not have an adverse effect on other components of a reaction mixture, when used in amounts sufficient to destabilize at least one duplex. For example, a duplex denaturant should not inhibit the activity of enzymes, such as polymerase or ligase, if activity of such enzymes is desired.

If the duplex-binding ligand is also a duplex-modifying reagent (e.g., a restriction enzyme, a ligase, and the like) other methods of detection are possible. For example, contacting a target:capture moiety duplex with a duplex modifying agent such as a duplex-selective restriction enzyme can result in selective modification of the duplex, but no modification of the unbound target or unbound capture moiety. With an appropriate choice of target and capture moiety, the target is detected by detecting modification of the capture moiety or the target sequence. In an exemplary embodiment, the capture moiety is labelled with a detectable label such as are known in the art, and a target strand is hybridized to the capture moiety. The target:capture moiety intermolecular duplex thus formed is then cleaved by a restriction enzyme. Detection of the labelled fragments of the capture moiety would thereby detect the presence of the target sequence of interest.

Although in preferred embodiments the capture moiety is bound to a solid support before being contacted with the target strand, in certain embodiments it may be preferred to contact the target strand with the capture moiety while both are in solution. The capture moiety:target strand duplex can then be immobilized on a solid support by contacting with an appropriately derivatized surface. For example, if capture moiety has been derivatized with biotin, as discussed supra, the capture moiety:target strand duplex can be immobilized by contacting it with a streptavidin-coated surface. Furthermore, if additional probes (e.g., secondary or reporter probes) are employed, they can be added before or after the capture moiety is immobilized to the solid support.

The methods of the invention are useful in detecting both natural and non-natural nucleic acid sequences. For example, the methods of the invention can be used to detect nucleic acids from the genome of an organism. In other embodiments, the methods of the invention can be used to detect the products of nucleic acid reactions such as strand cleavage, ligation, extension, modification, and the like. For example, in Example 3, infra, the use of nucleic acid capture moieties to detect the product of ligation of two probes is described. Thus, the methods of the invention can be used to detect nucleic acid sequences directly, by hybridization, or indirectly, by detection of amplification products from, for example, polymerase chain reaction or ligase chain reaction.

Figure 2:
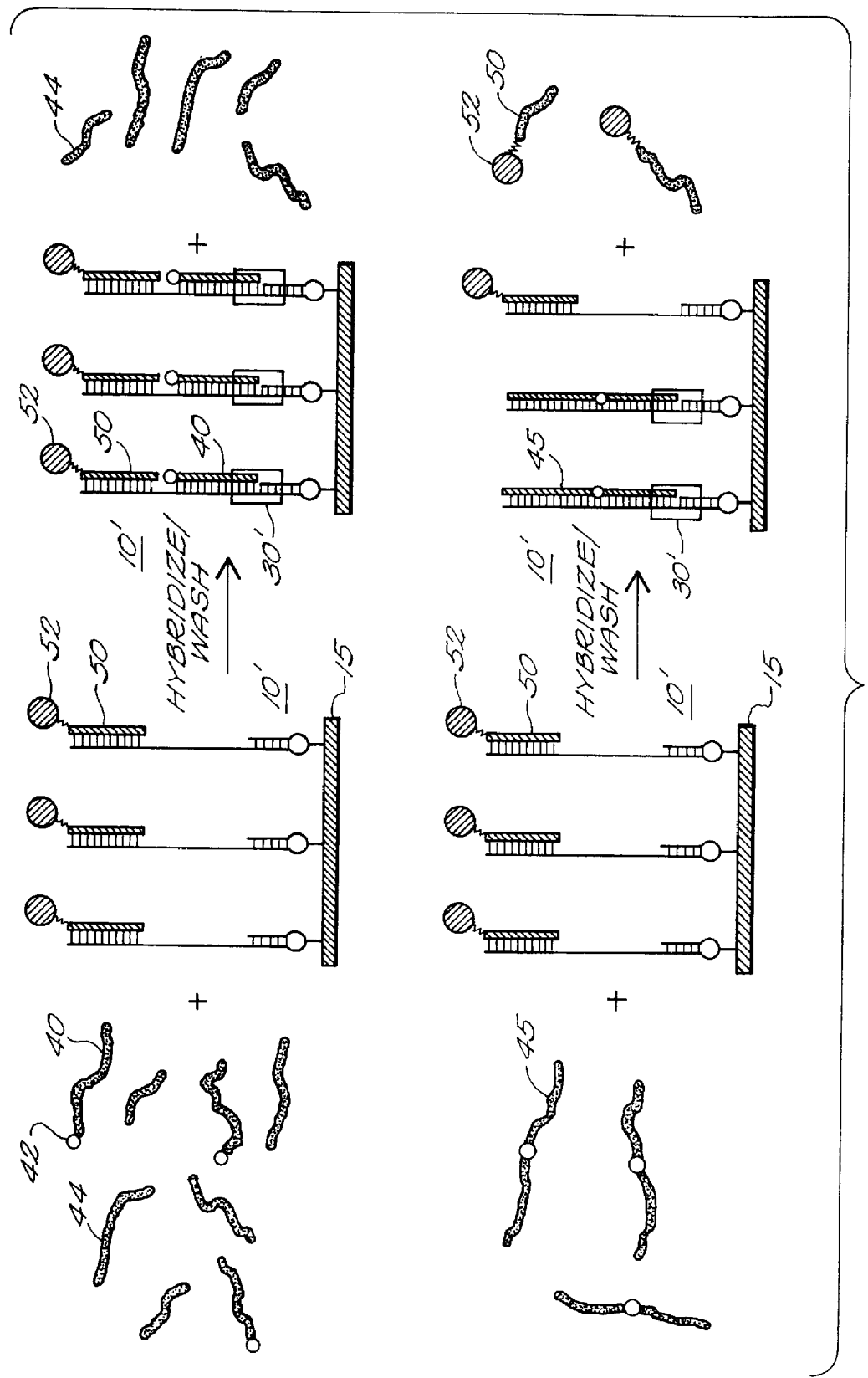
FIG. 2 is a reaction scheme showing detection of a target nucleic acid by displacement of a labelled secondary probe from a capture moiety.

Detection of target nucleic acid can be by a variety of methods, some of which are known in the art. In an illustrative embodiment, as shown in FIG. 2, a labelled secondary probe 50 with a detectable label 52 complementary to a target-complementary region of the capture moiety 10' (which is immobilized on insoluble support 15) can be hybridized to the capture moiety 10' in a reaction mixture. In this illustrative embodiment, the target nucleic acid is a ligated product 45 formed by ligation of probes 40 and 44 through phosphate 42. A sample suspected of containing the target nucleic acid is then introduced, under conditions such that any target sequence which is present will displace the secondary probe from the capture moiety. The upper reaction scheme of FIG. 2 depicts a reaction of a plurality of probes 40 (with phosphate 42) and 44 with a plurality of immobilized capture moieties 10', to which secondary probe 50 is hybridized. The capture moieties 10' are washed to remove unbound probes 40 and 44, and the amount of labelled secondary probe 50 remaining bound to the capture moieties 10' is measured. Illustratively, in the upper panel of FIG. 2 the probes 44 are not bound to the capture moieties 10' and the secondary probes 50 are not displaced by probes 40. The lower reaction scheme of FIG. 2 depicts the reaction of a plurality of ligated products 45 with capture moiety 10'. In the lower reaction scheme of FIG. 2, some of the ligated products 45 hybridize to the capture moieties 10', displacing secondary probes 50. A decrease in amount of secondary probe 50 bound to capture moiety 10', compared to a control well, indicates the presence of the target sequence 45. Alternatively, the amount of probe washed off in the washing step can be measured. The optional duplex-binding-ligand binding site 30' is also shown.

Figure 3:
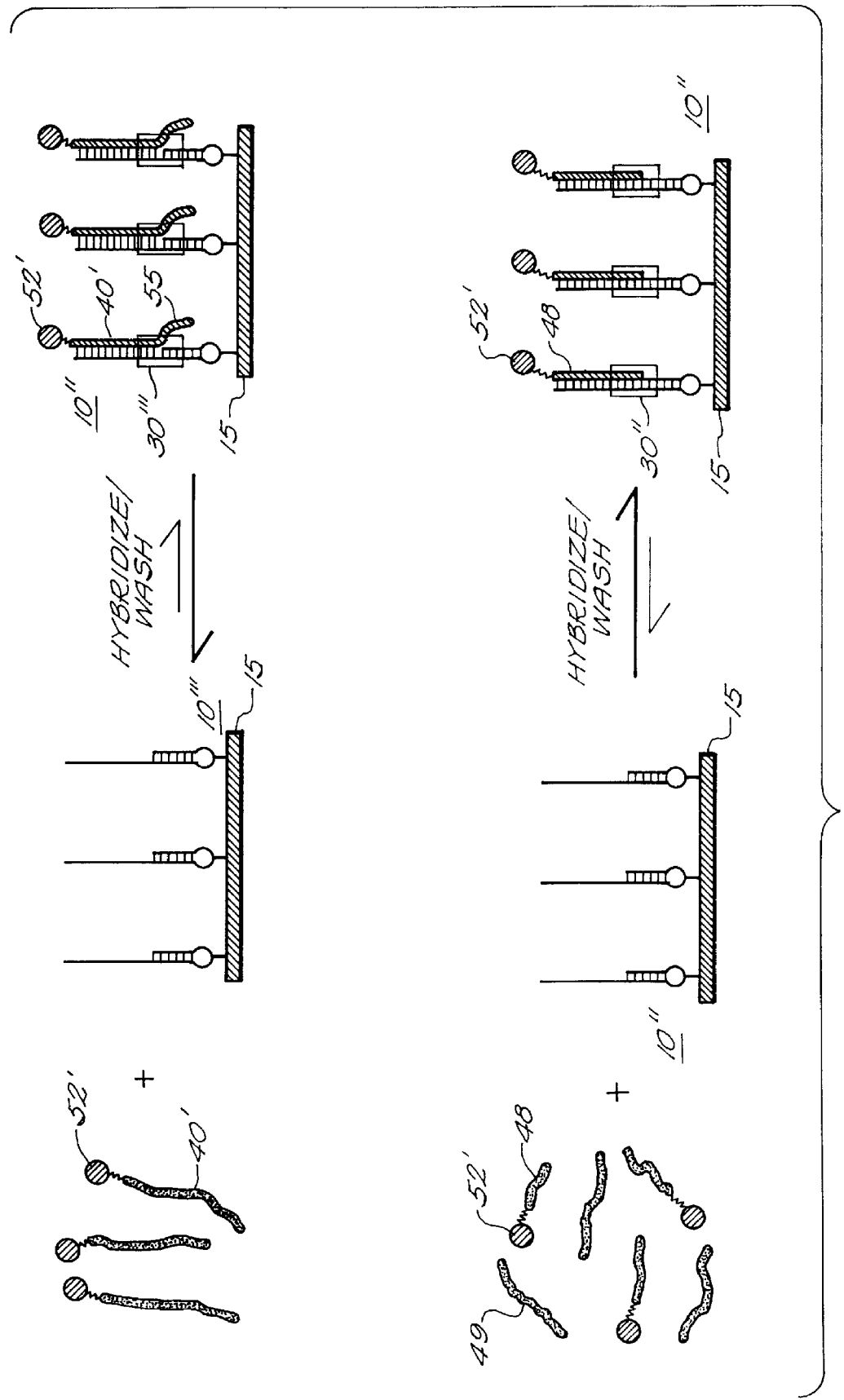
FIG. 3 is a reaction scheme showing discrimination between a cut target and an uncut target nucleic acid.

The capture moieties of the invention can also be used to discriminate between a target strand which has been cleaved (or otherwise modified) and an uncleaved strand, as shown in FIG. 3. The cut strand 48, which has a detectable label 52', is complementary to the capture moiety 10" (which is immobilized on insoluble support 15), while the uncut strand 40', which also has a detectable label 52', has a non-complementary overhang region 55 and is not effectively bound to the capture moiety 10". The target strand can be cut with, for example, a restriction enzyme. Thus, a sample is treated with a restriction enzyme and the products are incubated with an appropriately designed capture moiety. The upper panel of FIG. 3 illustrates that uncut strand 40' will not be stably bound to the capture moiety 10", as indicated by the equilibrium arrows showing that the hybridization of uncut strands 40' to capture moieties 10" is unfavorable. In the lower panel of FIG. 3, the equilibrium arrrows depict the favored binding of cut strands 48 to capture moieties 10", while the unlabeled fragments 49 are not bound to 10". By detecting the label 52' of bound products 48, the presence of the target sequence is detected. The optional duplex-binding-ligand binding site 30" is also shown. This scheme allows the capture moieties of the invention to be used for the detection of nucleic acid sequences which do not occur near the terminus of an intact target strand.

Figure 4:
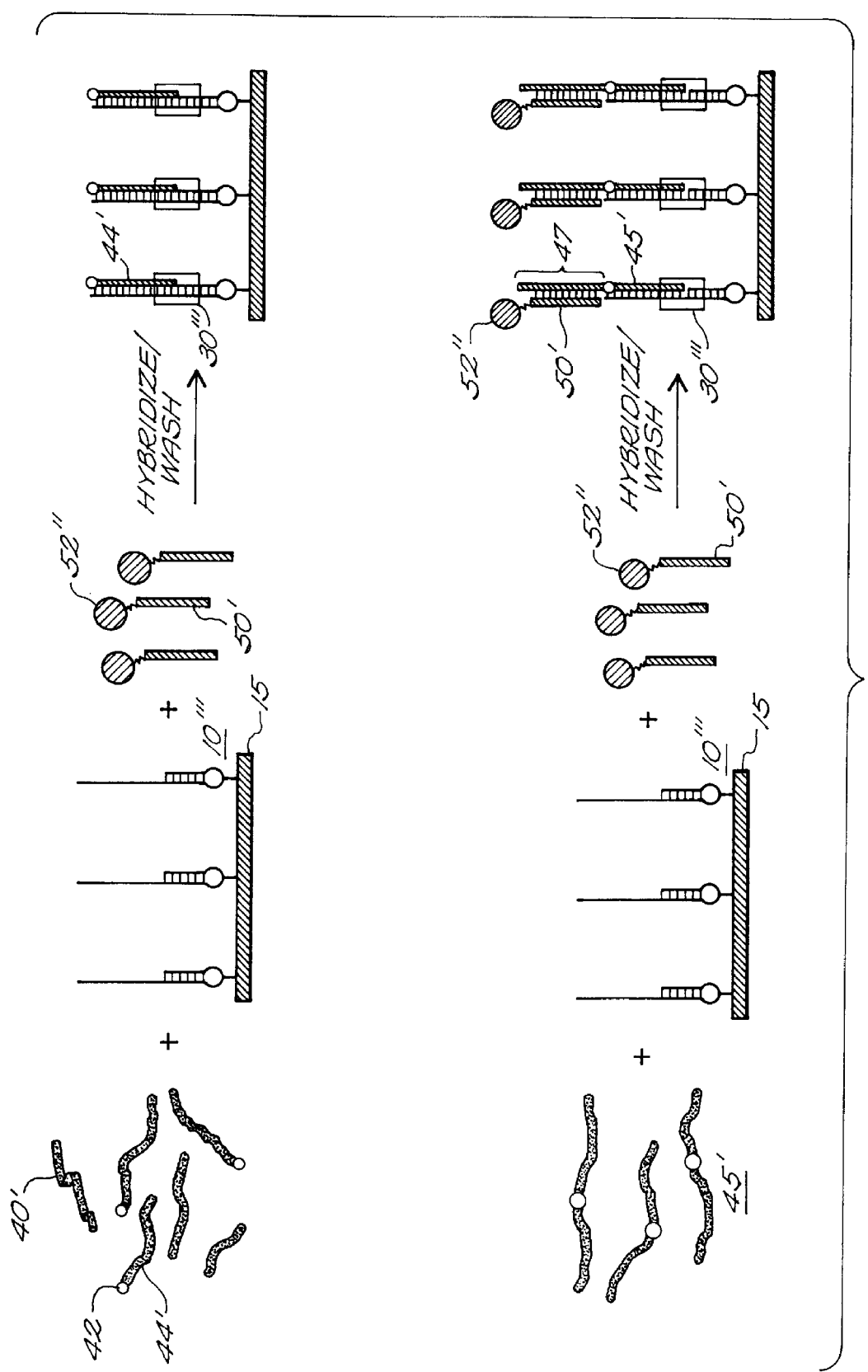
FIG. 4 is a reaction scheme showing detection of a ligated target nucleic acid by hybridization of a target-complementary secondary probe.

Another method of detection is shown in FIG. 4. In this embodiment, which is related to "sandwich" assays and is particularly useful for detection of products resulting from the ligation of probes 40' and 44' through phosphate 42, the capture moiety 10'" (which is immobilized on insoluble support 15) is complementary to a region of only one probe, illustratively probe 44'. A secondary probe 50' (called the detector probe) is labeled with a label moiety 52' and is complementary to a region of the probe 40'. As illustrated in the upper reaction scheme of FIG. 4, a plurality of unligated probes 44' hybridize to the capture moieties 10'", but are not labelled and so are not detected. Unligated probes 40' are washed away. As the lower reaction scheme of FIG. 4 illustrates, the ligation product 45' of the probes 40' and 44'" is bound to the capture moiety 10'" and the detector probe 50' hybridizes to region 47 of ligation product 45'; thus, only the ligated product is detected. The optional duplex-binding-ligand binding site 30'" is also shown.

It will apparent to the skilled artisan that other schemes for detecting target nucleic acids with the capture moieties of the invention are possible. For example, the target nucleic acid can be amplified before or after hybridization with the capture moiety to improve sensitivity.

Many labels are useful for detecting binding of target nucleic acids to capture moieties according to the present invention. Among methods known in the art are the use of radioisotopes (for example, $^{32}P$), fluorescent labels, enzymes (such as alkaline phosphatase and horseradish peroxidase, which can be used in calorimetric methods), antibodies, chemiluminescence, bioluminescence, and the like. In a preferred embodiment, a calorimetric method is used to detect target strand binding to a capture moiety. As previously described, labels can be attached to the capture moiety, the target nucleic acid, or a secondary probe, according to the desired method of detection. In certain embodiments, binding of a target strand to a capture moiety can be detected by chromatographic or electrophoretic methods, although this not preferred.

While the methods of the invention are easily performed manually, they are readily adapted to use with automated equipment. For example, robotic workstations are available which are capable of performing multiple analyses in parallel through the use of automated pipetting and automated plate readers for use with multi-well plates (described in more detail in Example 5, infra). Thus, in a preferred embodiment, the methods of the invention are performed with automated equipment. The use of automated equipment allows rapid, inexpensive analysis of single or multiple samples, for one or more target nucleic acid sequences.

In another aspect, the invention features a reaction mixture. In preferred embodiments, the reaction mixture includes one or more of the following: an immobilized hairpin, a solid or insoluble support, a non-immobilized hairpin, a target nucleic acid strand, a sequence-specific duplex-binding ligand, a non-sequence-specific duplex-binding ligand, a duplex-binding ligand which does not create or cleave any covalent bond, a duplex denaturant, a standard. In preferred embodiments, the reaction mixture is a solution.

In another aspect, the invention features a kit for the detection of a target nucleic acid. In preferred embodiments, the kit includes one or more of the following: an immobilized hairpin, a non-immobilized hairpin, a solid or insoluble support, a standard, a sequence-specific duplex-binding ligand, a non-sequence-specific duplex-binding ligand, a duplex-binding ligand which does not create or cleave any covalent bond, a duplex denaturant, instructions for use. The term "standard", as used herein, refers to a nucleic acid strand which is pre-selected to be substantially complementary to a single-stranded region of a capture moiety.

Exemplification

EXAMPLE 1

To test the ability of a nucleic acid hairpin capture moiety to discriminate between a "cut" oligonucleotide and an intact oligonucleotide under varying conditions of duplex-binding ligand and duplex denaturant, the following experiments were performed.

The radioisotopically-labelled 13-mer Probe 1 (the "cut" probe) 5'-CAGCG CGTTT TAG-3' (SEQ ID NO. 3) and 17-mer Probe 2 (the "uncut" probe) 5'-CAGCG CGTTT TAGCT TA-3' (SEQ ID NO. 4) were synthesized by standard protocols on a commercially available oligonucleotide synthesizer (Applied Biosystems ABI-380B). The immobilized nucleic acid hairpin was provided in the following manner: 1 mg of prewashed streptavidin-coated magnetic beads (available from Dynal) in 200 µl of BN buffer (1M NaCl/1 mM EDTA/0.025% Triton-X 100/10 mM Tris HCl, pH 7.5) was incubated with 500 pmol of the biotinylated hairpin (synthesized on an DNA synthesizer; the biotinylated bases were obtained from Glen Research) for one hour at room temperature with gentle rotation. The biotinylated hairpin had the following structure:

SEQ ID NO. 5

The hairpin and probe were chosen so that hybridization of the complementary probe with the hairpin forms a binding site for the duplex-binding ligand Actinomycin D (e.g., AGCT). The beads were then washed three times with BN buffer to remove unattached hairpin. Separate experiments with radiolabelled biotinylated hairpin established that about 20% (200 pmol) of the hairpin was bound to the beads.

For each experiment, 20 µg of beads with immobilized hairpin (about 2 pmol hairpin per experiment) was incubated with 20,000 CPM (about 2 fmol) in 20 µl of BN buffer for one hour. The beads were then washed three times with buffer containing urea and/or Actinomycin D at varying concentrations (see FIG. 5). The beads were then removed from the buffer with a magnet. Cerenkov counting of the beads and of the combined buffer and washes on a scintillation counter allowed calculation of the percent binding as CPM(beads)/[CPM(beads)+CPM(buffer)].

Figure 5A:
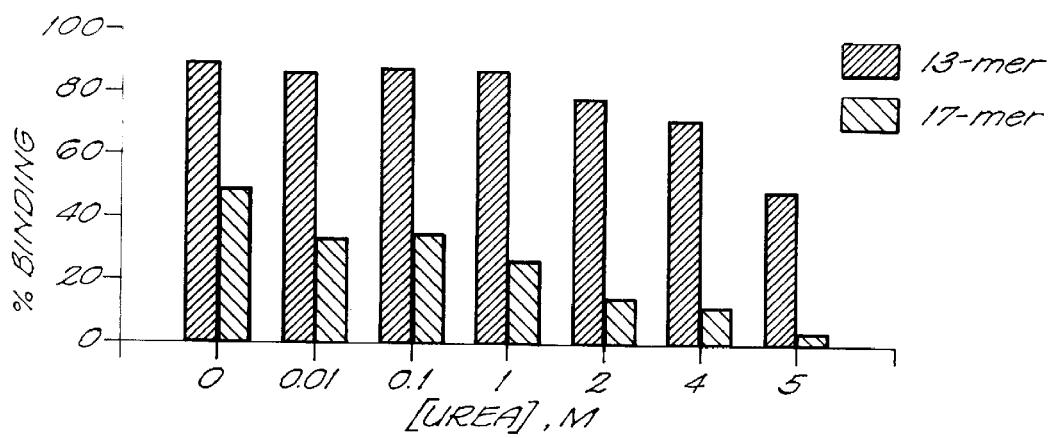
FIGS. 5A–5C are bar graphs showing the binding efficiency of cut and uncut target nucleic acid in varying conditions.
Figure 5B:
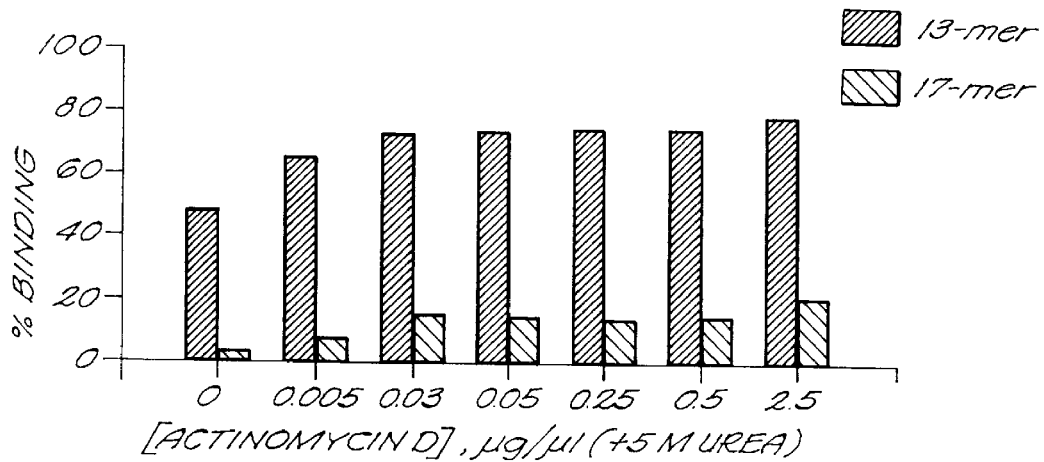
Figure 5C:
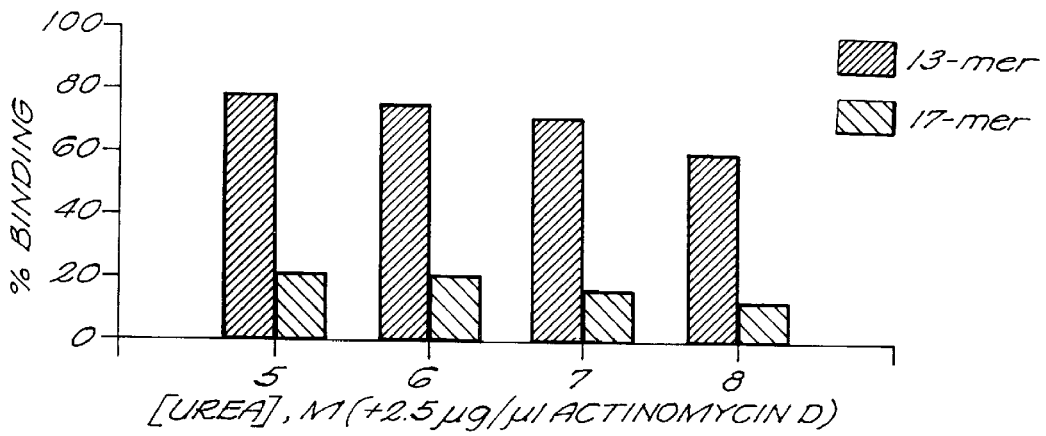

The results are shown in FIG. 5. It is clear that, as expected, as the concentration of a duplex denaturant (urea) is increased, the amount of bound oligonucleotide decreases (FIG. 5A). Importantly, binding of the "uncut" 17-mer drops off more sharply than binding of the "cut" 13-mer, so discrimination between the cut and uncut oligonucleotides increases at higher duplex denaturant concentrations. At a fixed concentration of urea, increasing amounts of Actinomycin D (a duplex-binding ligand) result in increased binding of both the cut and uncut oligonucleotides, and discrimination between the two oligonucleotides decreases (FIG. 5B). This result is also expected. Finally, FIG. 5C shows the effect of holding the concentration of Actinomycin D constant while varying the concentration of urea; the figure demonstrates that oligonucleotide discrimination under these conditions is highest at about 8M urea.

These results clearly show that cut and uncut oligonucleotide can be discriminated, and that the level of discrimination can be adjusted by changing the concentration of duplex-binding ligand or duplex denaturant.

EXAMPLE 2

The effect of wash buffer salt concentration on oligonucleotide binding, and the ability of the hairpin moiety to discriminate between a complementary and a non-complementary oligonucleotide, were tested in the following experiments.

The 13-mer Probe 1 (SEQ ID NO. 3), the 17-mer Probe 2 (SEQ ID NO. 4), and the hairpin capture moiety were prepared as in Example 1. The non-complementary 20-mer 5'TTATA ATTAA CCGGT ATATA-3' (SEQ ID NO. 6) was also synthesized by standard methods on an automated DNA synthesizer. Binding experiments were performed as described above, except that the beads were washed with 3 wash buffers contained decreasing salt concentrations; the first wash buffer had 1M NaCl, the second wash was with 0.1M NaCl, and the third wash was with 0.01M NaCl. None of the wash buffers contained urea or Actinomycin D.

Figure 6:
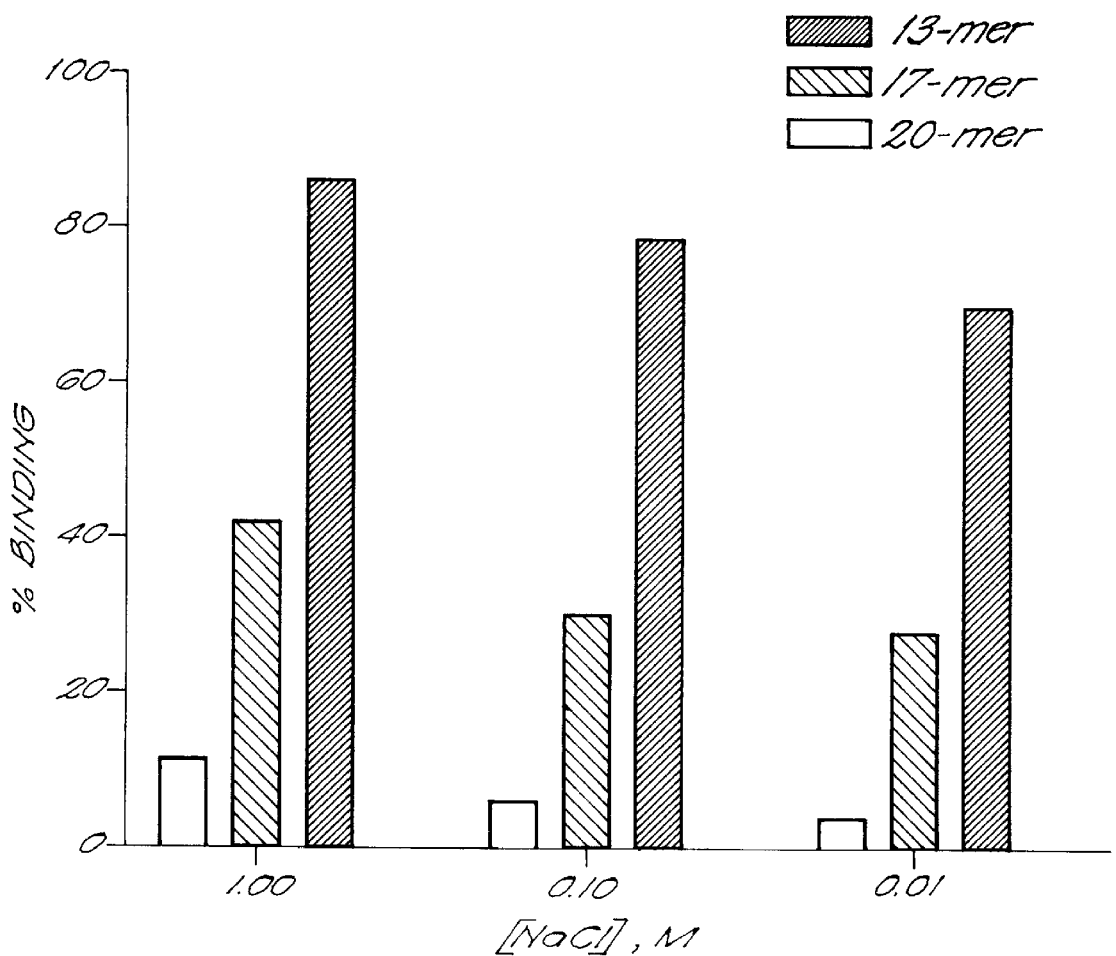
FIG. 6 is a bar graph showing effects of wash buffer salt concentration on binding efficiency.

The effect of varying wash buffer salt concentration on complementary/non-complementary discrimination is shown in FIG. 6. After the first wash, at high salt concentration, binding of the complementary oligonucleotide is greatest, as expected; the 17-mer has a 4-base segment which cannot bind effectively to the hairpin capture moiety and which destabilizes duplex formation. The subsequent washes at lower salt concentrations result in some washing off of all the oligonucleotides, but discrimination between the complementary oligonucleotide and the non-complementary oligonucleotide is improved. The improved discrimination stems from the large decrease in binding of the noncomplementary oligonucleotide, while the binding of the complementary oligonucleotide is only slightly decreased. Discrimination between the complementary 13-mer and the 17-mer also improves when the salt concentration decreases from 1M to 0.1M. Even after the low-salt wash about 70% of the complementary strand remains bound to the capture hairpin.

The results of this Example, taken together with the results of Example 1, demonstrate that the concentrations of salt (in the wash buffer), duplex-binding ligand, and duplex denaturant can be manipulated to attain optimal sensitivity or optimal selectivity (discrimination), or a balance between sensitivity and selectivity. This experiment also shows that the binding of target to the hairpin moiety is strong enough to survive relatively high-stringency washes.

EXAMPLE 3

The ability of the capture moiety to discriminate between a complementary target strand and a non-complementary strand was tested in the following experiments. The effect of an overhanging "tail" on the target strand was also tested.

The hairpin capture moiety used in Example 1 was incubated with one of three oligonucleotides: the 13-mer complementary strand (SEQ ID NO. 3), a 22-mer complementary strand 5'-GGCGT TAACC AGCGC GTTTT AG-3' (SEQ ID NO. 7), and a non-complementary 26-mer strand 5'-TACCG GAAGG AATTC TTCGT GCATG A-3' (SEQ ID NO. 8). The experiments were performed as described in Example 1. The probes were tested at several copy numbers. The results are shown in FIG. 7.

Figure 7A:
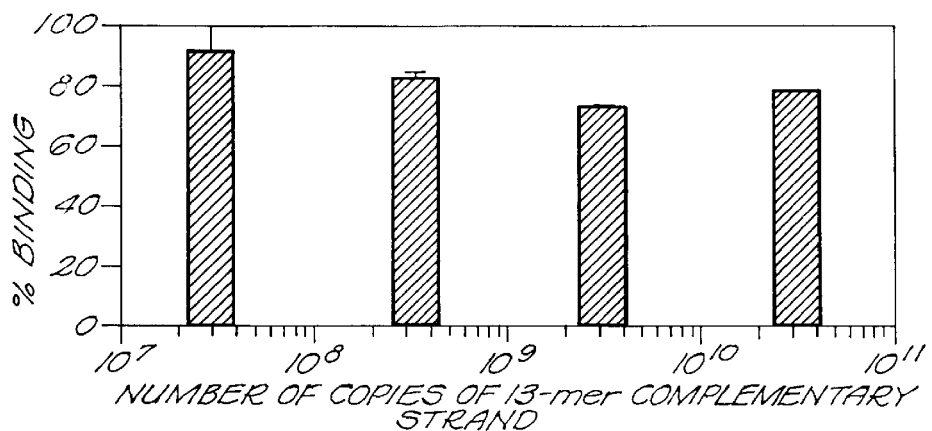
FIGS. 7A–7C are bar graphs showing the effect of target copy number on binding efficiency.
Figure 7B:
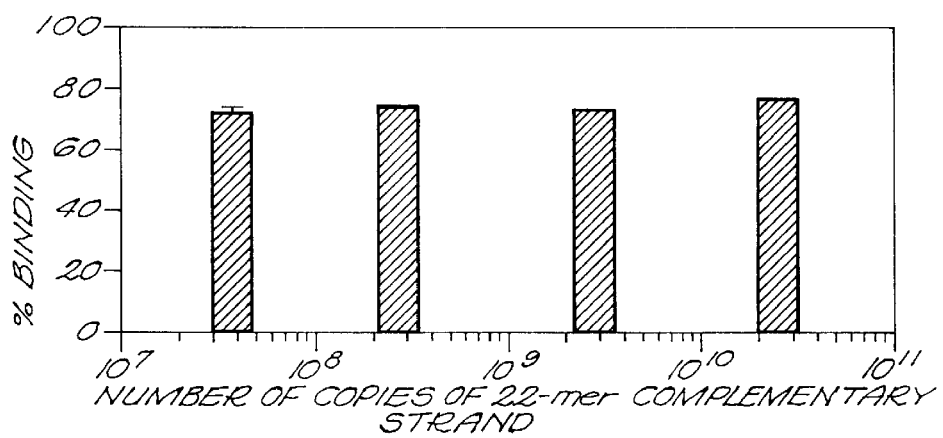
Figure 7C:
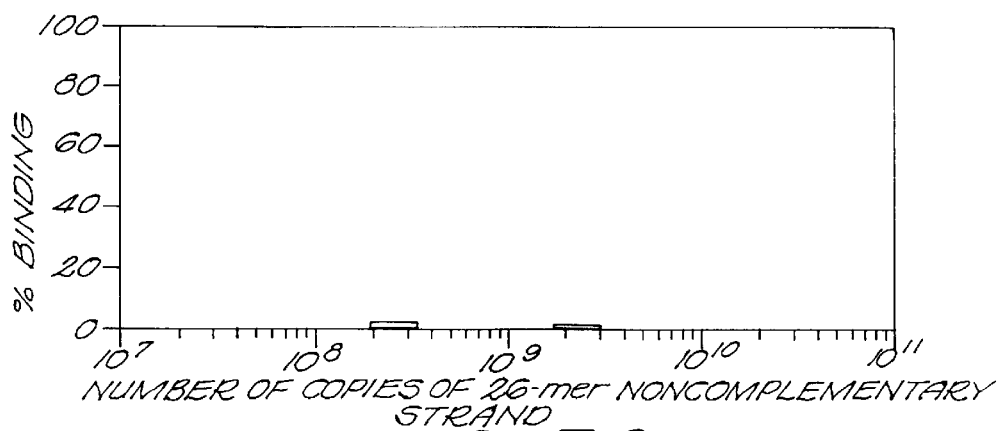

As shown in FIGS. 7A and 7B, the complementary strands (both the 13-mer and the 22-mer, which has an unpaired 9-base "tail") bind well to the capture hairpin. This result shows that the 9-mer "tail", which is not close to the "stem" or intramoecular duplex region of the capture moiety, has very little effect on target binding efficiency (in contrast to the "uncut" probe of Example 2, which had an unpaired end close to the stem of the capture moiety and which was significantly destabilized). The 26-mer non-complementary probe, as expected, shows very little binding to the capture moiety (<2%) (FIG. 7C). These results demonstrate that the capture moiety can efficiently discriminate between target and non-target sequences.

EXAMPLE 4

The ability of the capture moieties to capture and detect the products of a ligation reaction was demonstrated in the following example.

The target sequence was a 32-mer 5'-ATTTT TTGCA AATTT TTATT TGCCC GAGTA TA-3' (SEQ ID NO. 9) which corresponds to the E. coli rhsA gene. The two probes complementary to the product, probe 1 (7-mer) and probe 2 (15-mer), are shown below:

Probe 1: 5'-TTATT TGCCC GAGTA TA-3' SEQ ID NO. 10

Probe 2: 5'-ATTTT TTGCA AATTT-3' SEQ ID NO. 11

Probe 1 was 5'-phosphorylated with $^{32}$P following a standard kinasing protocol. The ligation reactions were performed in a microcentrifuge tube with 0.1 nmol Probe 2 and 20,000 CPM Probe 1 (about 1 fmol) in buffer (50 mM Tris-HiCl, pH 7.8, 10 mM MgCl$_2$, 10 mM dithiothreitol, 25 μg/ml bovine serum albumin, 1 mM ATP), total volume 20 μl. The target concentration was varied from 0.1 μM to 1 fM in 10-fold steps. Samples were annealed by heating to 90° for 5 minutes, and then cooled to room temperature. T4 ligase (400 units) was added (except to the no enzyme control) and the samples incubated at 37° for 2–4 hours. The ligase was inactivated by heating to 90° for 5 minutes.

20 μg of streptavidin-coated magnetic microbeads in 20 μl of BN buffer were then added to the ligation reaction mixture. The beads were previously derivatized with the biotinylated hairpin capture moiety shown below:

SEQ ID NO. 12

The beads had a total of about 4 pmol of immobilized hairpin capture moiety. The samples were incubated for 20–30 minutes at room temperature with gentle rotation, and then were separated from the buffer with a magnet and washed three times with BN buffer. The products were then separated by polyacrylamide gel electrophoresis. Films were exposed for 24 hours. Control samples which were not treated with the hairpin capture moiety were also analyzed.

Figure 8A:
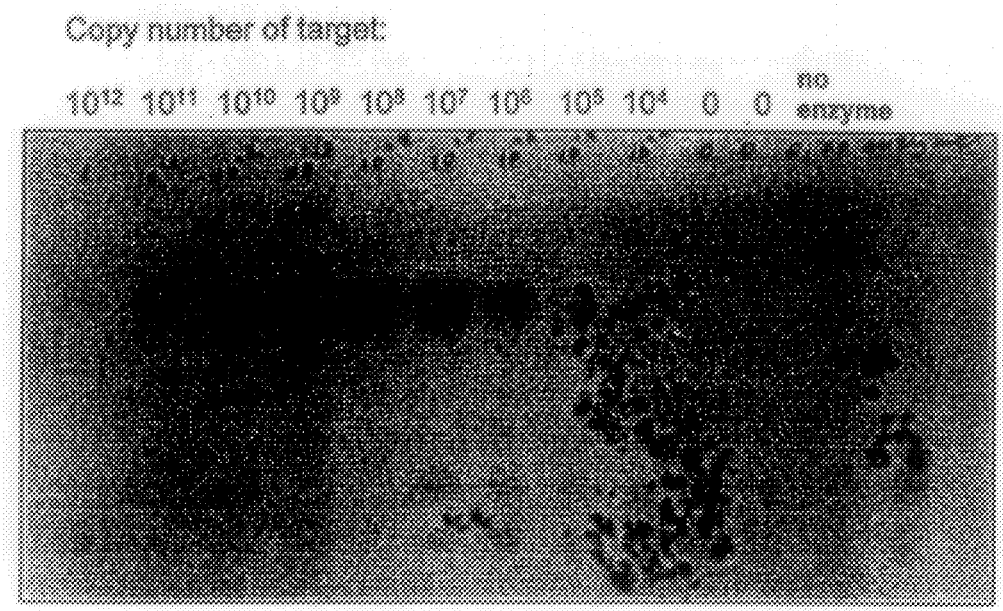
FIG. 8 is a gel showing the detection of ligated products by a hairpin capture moiety.
Figure 8B:
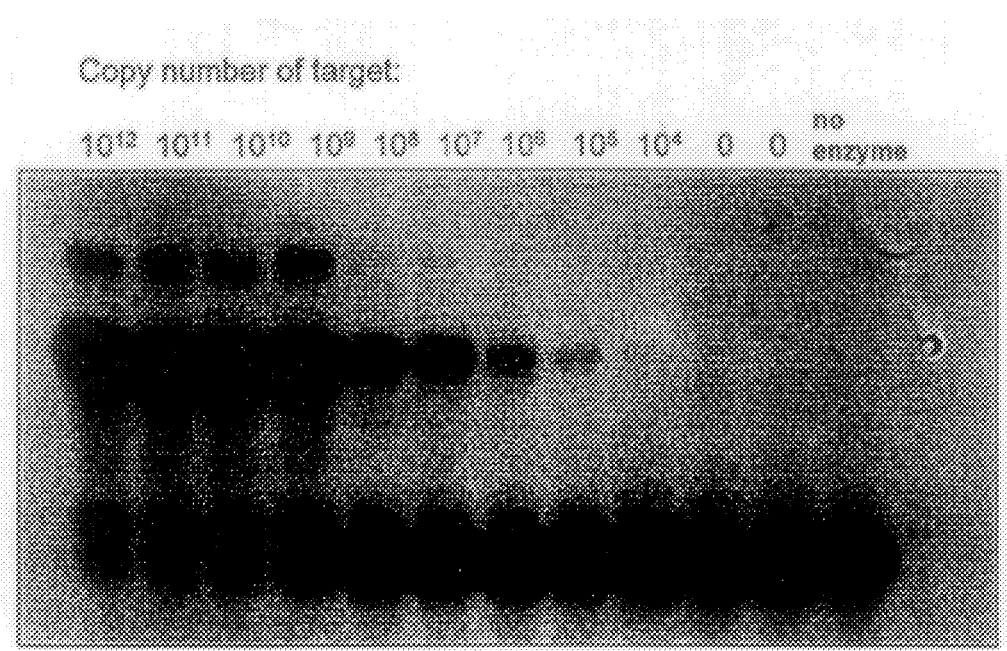
Figure 9A:
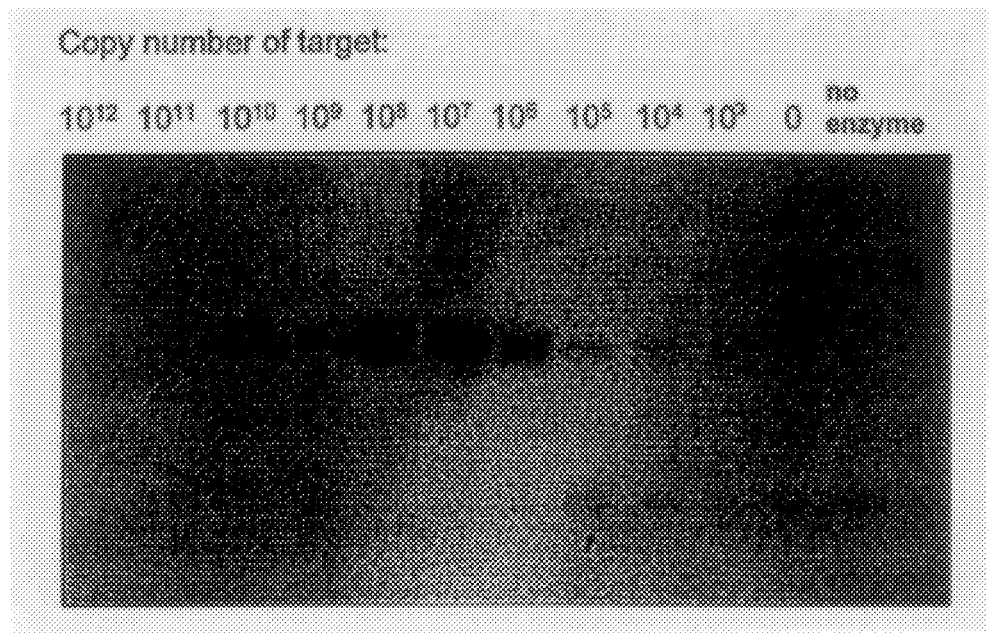
FIG. 9 is another gel showing the detection of ligated products by a hairpin capture moiety.
Figure 9B:
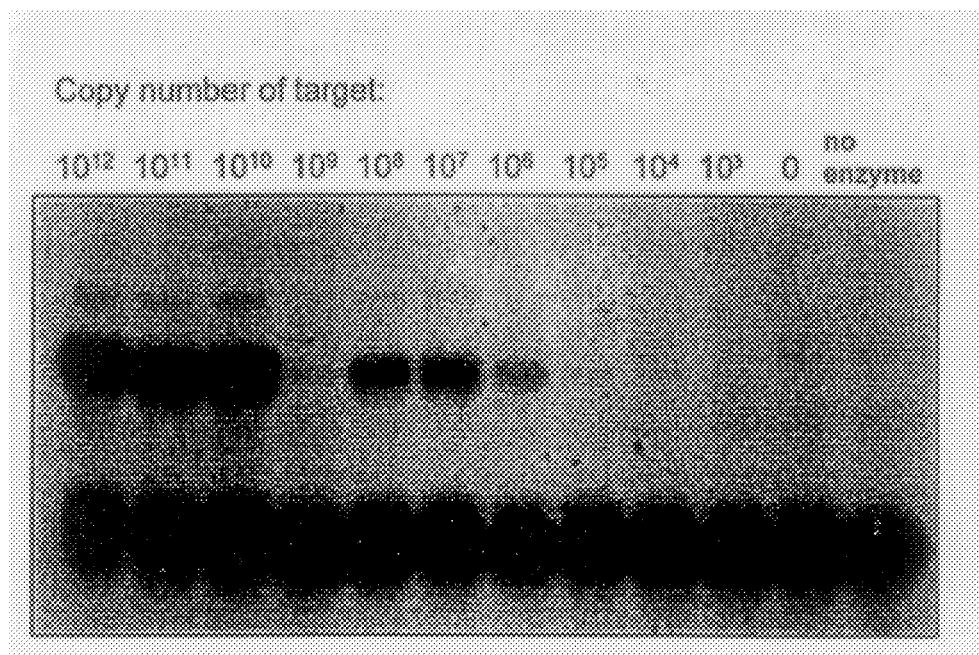

The results are shown in FIGS. 8 and 9. The bottom panel of FIG. 8 shows the band pattern of the reaction mixture before treatment with the hairpin capture moiety (control mixture). The lower band is unreacted probe; the main upper band is the ligated product. The small band at high copy numbers is an artifact. Ligated product is visible at $10^4$ copies of target. The upper panel of FIG. 8 shows the band pattern of the reaction products bound to the capture moiety. Very little unligated probe is seen, demonstrating the high selectivity of the system for the ligated product. Furthermore, the sensitivity of the system is almost the same as in the control mixture (lower panel), namely about $10^4$–$10^5$ copies of target (the grainy pattern seen in several lanes of the upper panel is an unrelated artifact). Note that at high target copy number the amount of ligated product captured by the hairpin decreases; this is believed to be due to the presence of excess target, which competes for the ligated product.

FIG. 9 shows a similar experiment performed with 800 units of T4 ligase. The results are similar to FIG. 8. The lane labelled "$10^9$" in the lower panel resulted from a flawed experiment.

EXAMPLE 5

This Example describes the use of multi-well plates for automated screening of samples for multiple target nucleic acid sequences.

Biotinylated DNA hairpins are synthesized according to the methods described in Example 1. One DNA hairpin sequence is synthesized for each target sequence of interest. For example, in screening for cystic fibrosis, several sequences which correspond to different mutations and are diagnostic for the disease would be used.

Each well of a 96-well plate is coated with streptavidin as described in, for example, U.S. Pat. No. 5,374,524 to Miller, and a plurality of biotinylated hairpins of one sequence are immobilized in each well. Unbound hairpins are removed by washing with buffer, and the prepared 96-well plate is placed in a robotic workstation. The workstation is programmed to add 100 μl of buffer to each well. The buffer contains urea (5M) and Actinomycin D (400 μM). Addition of buffer is followed by addition of 10 μl of a solution of sample DNA. The 96-well plate is incubated at room temperature for one hour, and the reaction mixture is then removed from each well by automated pipet. The wells are rinsed three times with buffer to remove unbound DNA. Then a solution containing a secondary probe, which is complementary to a region of the target sequence and has been labelled by covalent attachment of alkaline phosphatase according to well-known techniques, is added, The samples are again incubated, and the unhybridized probe is removed. The wells are rinsed with buffer and then treated with a solution of BCIP (5-bromo-4-chloro-3-indolylphosphate) and NBT (nitroblue tetrazolium). Wells having hairpins which bound to the sample DNA will develop a blue color which can be read by a conventional plate reader.

This assay is rapid, specific, uses standard equipment, and can easily be modified to detect any desired target nucleic acid.

Those skilled in the art will recognize, or be able to ascertain using no more than routine experimentation, numerous equivalents to the specific procedures described herein. Such equivalents are considered to be within the scope of this invention and are covered by the following claims.

The contents of all references and patent applications described herein are hereby incorporated by reference.

Other embodiments are within the following claims.

What is claimed is:

1. A method of promoting the hybridization of a target single-stranded nucleic acid and a nucleic acid capture moiety comprising:

a) providing a unimolecular nucleic acid capture moiety having a double-stranded region with a terminal base and an adjacent single-stranded region, the terminal base of the double-stranded region being all or part of a duplex-binding-ligand binding site, and said single-stranded region being capable of hybridizing to said target nucleic acid, wherein said unimolecular nucleic acid capture moiety is bound to a solid support;

b) forming a reaction mixture comprising said target single-stranded nucleic acid, said nucleic acid capture moiety, and a duplex-binding ligand, under conditions such that the target single-stranded nucleic acid and the nucleic acid capture moiety can hybridize; and c) allowing said target single-stranded nucleic acid to hybridize to said nucleic acid capture moiety such that said duplex-binding ligand binds to the intermolecular duplex thereby formed, such that the hybridization of the target single-stranded nucleic acid and the nucleic acid capture moiety is promoted.

2. The method of claim 1, wherein a first base pair of a duplex formed by the target single-stranded nucleic acid and the single-stranded region of the nucleic acid capture moiety encodes part of the duplex-binding-ligand binding site.

3. The method of claim 1, wherein the nucleic acid capture moiety comprises a nucleic acid hairpin.

4. The method of claim 1, wherein stability of the intermolecular duplex is increased by base stacking between the terminal base of the nucleic acid capture moiety and a terminal base of the target single-stranded nucleic acid which forms a part of the intermolecular duplex.

5. A method of detecting a target single-stranded nucleic acid sequence, comprising:
   a) providing a nucleic acid capture moiety comprising a structure A-B-C-D wherein
      A is a nucleic acid sequence;
      B and D are nucleic acid sequences which are capable of hybridizing to each other to form an intramolecular duplex; and
      C is a linker which covalently links B and D;
      wherein A is substantially complementary to a target single-stranded nucleic acid sequence and the nucleic acid capture moiety is immobilized on an insoluble support;
   b) forming a reaction mixture comprising said target single-stranded nucleic acid and said nucleic acid capture moiety under conditions such that a B:D intramolecular duplex can form and the target single-stranded nucleic acid and the nucleic acid capture moiety can hybridize; and
   c) detecting the presence or absence of hybridization of the target nucleic acid and the nucleic acid capture moiety;
      such that the target single-stranded nucleic acid is detected.

6. The method of claim 5, wherein the terminal base of D comprises all or part of a duplex-binding-ligand binding site.

7. The method of claim 5, wherein said reaction mixture further comprises a duplex-binding ligand.

8. The method of claim 7, wherein the duplex-binding ligand does not covalently modify any duplex.

9. The method of claim 5, wherein stability of the intermolecular duplex is increased by base stacking between the terminal base of the nucleic acid capture moiety and a terminal base of the target single-stranded nucleic acid which forms a part of the intermolecular duplex.

10. The method of claim 5, wherein the detecting step comprises detecting a secondary probe.

11. The method of claim 10, wherein the secondary probe comprises a label.

12. A method of detecting a target single-stranded nucleic acid sequence, comprising:
   a) providing a nucleic acid capture moiety comprising a structure A-B-C-D wherein
      A is a nucleic acid sequence;
      B and D are nucleic acid sequences which are capable of hybridizing to each other to form an intramolecular duplex; and
      C is a linker which covalently links B and D;
      wherein A is substantially complementary to a target single-stranded nucleic acid sequence and the nucleic acid capture moiety is immobilized on an insoluble support;
   b) forming a reaction mixture comprising said target single-stranded nucleic acid and said nucleic acid capture moiety under conditions such that a B:D intramolecular duplex can form and the target single-stranded nucleic acid and the nucleic acid capture moiety can hybridize to form an intermolecular duplex, wherein the intermolecular duplex comprises a duplex-binding-ligand binding site; and
   c) detecting the presence or absence of hybridization of the target nucleic acid and the nucleic acid capture moiety;
      such that the target single-stranded nucleic acid is detected.

13. The method of claim 12, wherein hybridization of the target single-stranded nucleic acid to the nucleic acid capture moiety forms a nicked duplex.

14. The method of claim 12, wherein the duplex-binding-ligand binding site does not include a nick.

15. The method of claim 12, wherein the reaction mixture further comprises a duplex-binding ligand.

16. The method of claim 15, wherein the duplex-binding ligand is sequence-specific.

17. The method of claim 15, wherein the duplex-binding ligand does not covalently modify any duplex.

18. The method of claim 12, wherein stability of the intermolecular duplex is increased by base stacking between the terminal base of the nucleic acid capture moiety and a terminal base of the target single-stranded nucleic acid increases stability of the intermolecular duplex.

19. A method of promoting the hybridization of a target single-stranded nucleic acid and a nucleic acid capture moiety comprising:
   a) providing a unimolecular nucleic acid capture moiety having a double-stranded region and an adjacent single-stranded region, said single-stranded region being capable of hybridizing to said target nucleic acid, wherein said unimolecular nucleic acid capture moiety is bound to a solid support;
   b) forming a reaction mixture comprising said target single-stranded nucleic acid, said nucleic acid capture moiety, and a duplex-binding ligand, under conditions such that the target single-stranded nucleic acid and the nucleic acid capture moiety can hybridize; and
   c) allowing said target single-stranded nucleic acid to hybridize to said nucleic acid capture moiety to form an intermolecular duplex, wherein the intermolecular duplex comprises a duplex-binding-ligand binding site, such that said duplex-binding ligand binds to said duplex-binding-ligand binding site,
      such that the hybridization of the target single-stranded nucleic acid and the nucleic acid capture moiety is promoted.

20. The method of claim 19, wherein the nucleic acid capture moiety comprises a nucleic acid hairpin.

21. The method of claim 19, wherein the duplex-binding ligand does not covalently modify any duplex.

22. The method of claim 19, wherein the duplex-binding-ligand binding site does not include a nick.

23. The method of claim 19, wherein stability of the intermolecular duplex is increased by base stacking between the terminal base of the nucleic acid capture moiety and a terminal base of the target single-stranded nucleic acid which forms a part of the intermolecular duplex.

24. A method of capturing a target single-stranded nucleic acid sequence from a sample, comprising:
   a) providing a nucleic acid capture moiety comprising a structure A-B-C-D wherein
      A is a nucleic acid sequence;
      B and D are nucleic acid sequences which are capable of hybridizing to each other to form an intramolecular duplex; and C is a linker which covalently links B and D;

wherein A is substantially complementary to the target single-stranded nucleic acid sequence and the nucleic acid capture moiety is immobilized on an insoluble support;

b) forming a reaction mixture comprising said target single-stranded nucleic acid and said nucleic acid capture moiety under conditions such that a B:D intramolecular duplex can form and the target single-stranded nucleic acid hybridizes to said nucleic acid capture moiety; and c) separating the target single-stranded nucleic acid hybridized to said nucleic acid capture moiety from the reaction mixture;

such that the target single-stranded nucleic acid is captured.

* * * * *